(12) United States Patent
DeSantis (10) Patent No.: US 11,607,228 B2
(45) Date of Patent: Mar. 21, 2023

(54) HEMOSTASIS PRESSURE DEVICE

(71) Applicant: CORDIS US CORP., Miami Lakes, FL (US)

(72) Inventor: Nicholas Andrew DeSantis, Fort Lauderdale, FL (US)

(73) Assignee: CORDIS US CORP., Miami Lakes, FL (US)

( * ) Notice: Subject to any disclaimer, the term of this patent is extended or adjusted under 35 U.S.C. 154(b) by 0 days.

(21) Appl. No.: 16/868,335

(22) Filed: May 6, 2020

(65) Prior Publication Data

US 2020/0352577 A1 Nov. 12, 2020

Related U.S. Application Data

(60) Provisional application No. 62/844,546, filed on May 7, 2019.

(51) Int. Cl.
| | |
|---|---|
| *A61B 17/132* | (2006.01) |
| *A61M 39/02* | (2006.01) |
| *A61B 17/00* | (2006.01) |
| *A61B 90/00* | (2016.01) |
| *A61B 17/12* | (2006.01) |

(52) U.S. Cl.
CPC ......... *A61B 17/1325* (2013.01); *A61M 39/02* (2013.01); *A61B 2017/0023* (2013.01); *A61B 2017/00893* (2013.01); *A61B 2017/00902* (2013.01); *A61B 2017/12004* (2013.01); *A61B 2090/0807* (2016.02); *A61B 2090/3937* (2016.02)

(58) Field of Classification Search
CPC .............. A61B 17/1322; A61B 17/132; A61B 17/1325; A61B 17/1327; A61B 17/135; A61B 17/1355; A61B 2017/00659; A61B 2017/00676; A61B 2017/12004; A61F 5/32; A61F 5/34; A61F 2013/00468; A61F 2013/00472
USPC ......................................... 606/201, 203, 204
See application file for complete search history.

(56) References Cited

U.S. PATENT DOCUMENTS

| | | | | |
|---|---|---|---|---|
| 5,690,672 | A | * | 11/1997 | Cohen ................ A61B 5/02233 606/203 |
| 2009/0005722 | A1 | * | 1/2009 | Jennings-Spring .......................... A61F 13/00021 604/20 |
| 2010/0280541 | A1 | * | 11/2010 | Lampropoulos ..... A61B 17/132 606/203 |
| 2012/0116444 | A1 | * | 5/2012 | Zodnik ................ A61B 17/135 606/202 |
| 2012/0191127 | A1 | * | 7/2012 | Guillot ............... A61B 17/1327 606/203 |

(Continued)

FOREIGN PATENT DOCUMENTS

WO WO-2020169573 A1 * 8/2020 ......... A61B 17/1325

*Primary Examiner* — Martin T Ton
(74) *Attorney, Agent, or Firm* — Arentfox Schiff LLP (57) ABSTRACT

A hemostasis pressure device is disclosed. In one embodiment, the hemostasis pressure device includes a reusable component and a disposable cuff. The disposable cuff includes a pre-inflated pad configured to be placed at an access site on a patient. A knob secured to the reusable component is configured to control the pressure applied to the pre-inflated pad, providing incremental, fine-tuned control of pressure applied to the access site to achieve patent hemostasis.

20 Claims, 5 Drawing Sheets

(56) References Cited

U.S. PATENT DOCUMENTS

2015/0119773 A1* 4/2015 Flannery .............. A61B 17/135
601/152
2015/0327870 A1* 11/2015 Fortson .............. A61B 17/0057
606/202

* cited by examiner

HEMOSTASIS PRESSURE DEVICE

BACKGROUND

Transradial, transulnar, and transfemoral are catheterization approaches which are used for both diagnostic and interventional procedures. In transradial and transulnar catheterization, an introducer sheath, and/or guidewire, and/or catheter is introduced into the radial or ulnar artery using an access site at a patient's wrist, as opposed the traditional transfemoral catheterization method, in which such devices are introduced at the femoral artery at an access site in the upper leg or groin region. Recently, transradial catheterization has gained increased popularity over traditional transfemoral catheterization. The popularity of transradial catheterization can be attributed to many benefits, including increased comfort for a patient, increased patient safety as there are fewer side effects (e.g., low bleeding and pseudoaneurysm), less hospital cost, and a rapid recovery time.

When a catheterization procedure is complete, any associated bleeding must be controlled until the patient's natural healing process, i.e., blood clotting, seals the access site to the blood vessel. Thus, as the catheter is withdrawn from the body, a device must maintain pressure against the puncture site until hemostasis is achieved. One potential complication following transradial or transulnar catheterization is artery occlusion, which can occur when too much pressure is applied to the puncture site and radial or ulnar artery blood vessel. In order to prevent radial or ulnar artery occlusion, the device can apply just enough pressure to stop bleeding at the puncture site while still allowing blood to flow through the radial or ulnar artery. This is known as patent hemostasis, and it allows the body's physiological process to stop bleeding at the access site while maintaining normal blood flow throughout blood vessels.

SUMMARY

The following embodiments and aspects thereof are described and illustrated in conjunction with systems, tools and methods which are meant to be exemplary and illustrative, and not limiting in scope.

In one aspect, a hemostasis pressure device is disclosed. The hemostasis pressure device includes a reusable component having an outer housing and an inner housing, and a disposable cuff positioned within the inner housing, the disposable cuff comprising a pre-inflated pad. The pre-inflated pad is configured to be placed at an access site of a patient. A knob is secured to the reusable component, the knob having a portion through which the access site can be viewed. The knob is configured to control pressure applied to the pre-inflated pad. The more precision involved in the control of applied pressure, the lower the risk of artery occlusion.

In another aspect, a hemostasis pressure device includes a strap configured to be placed at an access site of a patient, a hemostatic agent-infused pad secured to the strap and configured to be placed over the access site, and a plurality of air pocket blisters secured to the strap. One or more of the plurality of air pocket blisters are configured to be deactivated to reduce the pressure applied by the strap.

In addition to the exemplary aspects and embodiments described above, further aspects and embodiments will become apparent by reference to the drawings and by study of the following detailed description.

BRIEF DESCRIPTION OF THE DRAWINGS

Exemplary embodiments are illustrated in the drawings. It is intended that the embodiments and Figures disclosed herein are to be considered illustrative rather than restrictive.

DETAILED DESCRIPTION

In the following detailed description, reference is made to the accompanying Figures, which form a part thereof. In the Figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

I. Overview

Hemostasis pressure devices are disclosed herein. In one embodiment, a hemostasis pressure device includes a reusable component and a disposable cuff. In some embodiments, the reusable component comprises an outer frame and the disposable cuff comprises a flexible inner band. The flexible inner band includes a pre-inflated blister compression pad configured to be applied to the access site on an arm or wrist of a patient such that the blister compression pad adheres to the patient's wrist or arm but does not apply enough pressure by itself to stop bleeding at the access site. A knob may be secured to the reusable component, and controls an amount of pressure applied to the access site to stop bleeding without occluding underlying blood vessels via applying incremental or decremental pressure to the blister compression pad. The disclosed hemostasis pressure devices described herein allow for an incremental/decremental application of pressure to an access site on a patient. Advantageously, such incremental/decremental application of pressure to an access site provided by the disclosed hemostasis pressure devices provides for finely-tuned control of pressure application.

II. EXAMPLES

Figure 1:
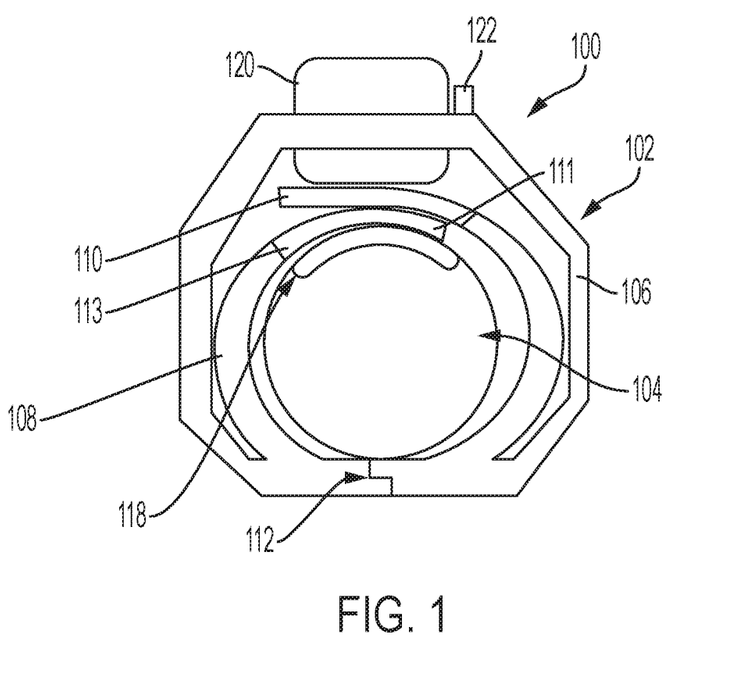
FIG. 1 depicts a side view of an example hemostasis pressure device, in accordance with an embodiment.

Referring to FIGS. 1-4, an example hemostasis pressure device 100 is disclosed. FIG. 1 depicts a side view of the hemostasis pressure device 100. The hemostasis pressure device 100 includes a reusable component 102 and a disposable cuff 104. The reusable component 102 may take the form of an outer frame. In some embodiments, the reusable component 102 may be made of a rigid material, or may be made of a substantially rigid material that still provides some flexibility. The reusable component 102 may comprise a durable polymer, for example. In some embodiments, the reusable component 102 may be made of a non-rigid, compliant material. In some embodiments, the material may be able to withstand autoclave, vaporized hydrogen peroxide (VHP), and/or other terminal sterilization and disinfection modalities. However, it should be understood that the reusable component could be constructed of any suitable material.

The embodiment depicted in FIG. 1 shows the reusable component 102 having an outer housing 106 and an inner housing 108. As shown in the embodiment of FIG. 1, the outer housing 106 surrounds the inner housing 108. The outer housing 106 is shown as having a substantially octagonal shape, however, it should be understood that the outer housing may take the form of a number of other shapes. For example, in some embodiments the outer housing 106 may comprise a generally circular or elliptical shape. In other embodiments, the outer housing 106 may comprise a double or pronged cable/cord, or a cable/cord with two ends shaped as a single strap and the middle of the cable/cord diverging such that the cable/cord forms a circular or hexagonal viewing window to allow for the user to continuously view the access site during use. The inner housing 108 is sized and shaped to receive a patient's arm or wrist therethrough, and in the embodiment of FIG. 1 is shown to comprise a generally circular or elliptical shape. In some embodiments, the reusable component 102 may include only an outer housing with no inner housing(s).

In some embodiments, the inner housing 108 is formed by a first end portion 110 overlapping a second end portion 111. In one embodiment, both the first end portion 110 and second end portion 111 may include a transparent material, or have a pronged shape or an open void within each component so that the user can see through the components to view the access site. The first and second overlapping end portions 110, 111 cause the incremental and decremental pressures applied by the knob to be distributed widely and evenly across at least the entirety of the access site location and/or the compression pad on the reusable component. One or both of the first and second end portions 110, 111 may include a marker 113, such as a color, line, graphic, or other feature to indicate correct positioning or alignment of the reusable component 102 and/or the disposable cuff 104 relative to one another, and/or relative to the access site of the patient. In one embodiment, the marker 113 may comprise arrows which point to each other when correctly aligned. In some embodiments, the marker 113 may include a plurality of markers. In some embodiments, the marker 113 may be positioned on a portion of the reusable component 102 and/or a portion of the disposable cuff 104, as will be described in more detail below.

In some embodiments, the reusable component 102 further includes a fastening mechanism 112 on the outer housing 106 and/or the inner housing 108 that allows the reusable component 102 to be opened and closed when being secured to or removed from a patient, if needed. Example fastening mechanisms include, but are not limited to, latches, locks, clamps, clips, hook and loop closures, buttons, snaps, hinges, and the like.

Figure 2:
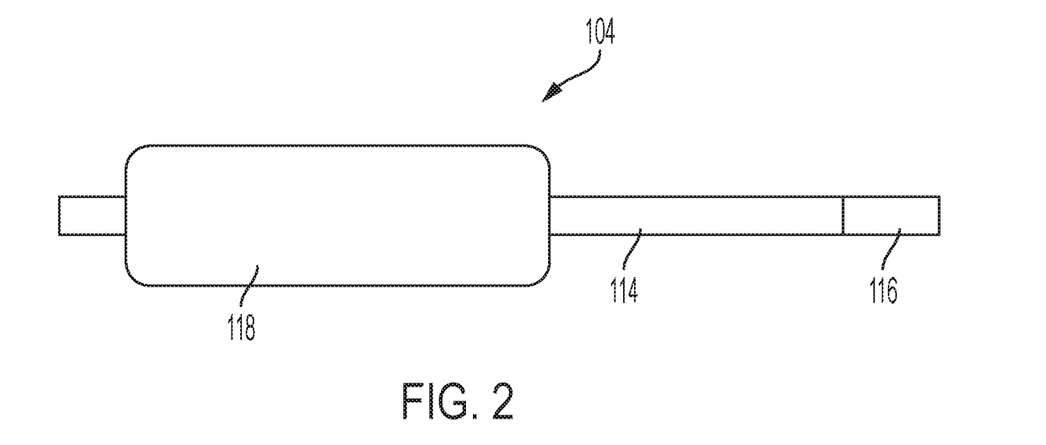
FIG. 2 depicts a disposable cuff of the device shown in FIG. 1, in accordance with an embodiment.

As noted above, the hemostasis pressure device 100 may further include a disposable cuff 104. The disposable cuff 104 is shown in FIG. 1 to be positioned within the inner housing 108 of the reusable component 102. The disposable cuff 104 may be positioned adjacent or on an inner surface of the inner housing 108 of the reusable component 102. FIG. 2 depicts a disposable cuff 104 of the device shown in FIG. 1. As shown in FIG. 2, the disposable cuff 104 comprises a flexible strap 114 including an adhesive 116 and a pre-inflated pad 118. The flexible strap 114 is configured to be placed around a wrist or arm of a patient, with the pre-inflated pad 118 positioned to cover the access site on the patient. In some embodiments, the flexible strap 114 is made of a thermoplastic elastomer material. Alternatively, the flexible strap 114 may be made of any suitable material, such as other plastic, rubber, or silicone materials, for example.

The adhesive 116 is used to affix one end of the strap to the other end of the strap, such that the strap 114 can be wrapped around and secured on the patient. It should be understood that in some embodiments, the adhesive 116 may be replaced with any other suitable fastening mechanism. Additionally, some embodiments may comprise a strap having no adhesive or other fastening mechanism.

The pre-inflated pad 118 may be a disposable, sterile pad that can be inflated to a predetermined pressure or filled to a predetermined volume. In one embodiment, the predetermined volume is a set value between about 1 and about 40 cubic centimeters (cc's). Further, in some embodiments, the size of the pre-inflated pad 118 may range from about 1 inch to about 3 inches in width, about 1 inch to about 5 inches in length, and about 1 mm to 40 mm in height. The size, volume, and pressure of the pre-inflated pad 118 may be variable and may be available to the user via a plurality of pre-inflated pads with different volumes and sizes available for selection by the user. The ideal volume and size of the pre-inflated pad 118 for use on the patient is dependent on a variety of factors such as patient-specific physiological factors (i.e. circumference of patient's wrist, circumference of patient's blood vessel(s), cardiovascular disease related factors that impact strength or constriction of blood vessels, abnormal blood flow volume or blood pressure, etc.), severity and size of access site wound, and/or complications that may arise during the catheterization procedure itself. The final pressure of the pre-inflated pad 118 on the patient's wrist should be less than the threshold pressure that results in radial or ulnar artery occlusion.

In some embodiments, the pad 118 may be made of silicone. In other embodiments, the pad 118 may be made of any suitable material, such as transparent polymers, polymer composites, or plastics, for example. In some embodiments, the pad 118 is made of a transparent material. Additionally, in some embodiments, the pad 118 may include or be coated with a hemostatic agent. The pre-inflated pad 118 may be integral with or attached to the flexible strap 114. In some embodiments, the flexible strap may be omitted and the pad 118 may be attached directly to the reusable component via adhesive or another suitable fastening mechanism.

Referring again to FIG. 1, a knob 120 may be secured to the reusable component 102. In one embodiment, the knob 120 is configured as a dial that can be manually rotated to incrementally control the pressure applied to the pre-inflated pad 118. As the knob 120 is rotated, the knob 120 moves in a downward direction toward the pre-inflated pad and access site, pressing against the first and second end portions 110, 111 of the inner housing 108. The pressing of the knob 120 increases the pressure applied to the inner housing 108 and thus also to the access site. Additionally, the rotation of the knob 120 increases or decreases the applied pressure incrementally. Therefore, the knob 120, in conjunction with the first and second end portions 110 and 111, and in conjunction with the pre-inflated pad 118 provide for improved fine-tune control of the pressure applied to the patient's access site. Fine-tune control of the knob 120 may be achieved by using both the device(s) described herein to stop bleeding at the wound site, in conjunction with a pulse oximeter, Doppler ultrasound device, or other commonly available blood flow measurement/diagnostic devices to ensure continuous blood flow throughout the patient's radial or ulnar artery and/or other blood vessels.

The knob 120 may also include a knob lock 122, which can lock the knob 120 in a specific position. The knob lock 122 may be any type of locking mechanism suitable for locking a control knob. In some embodiments, the knob lock 122 is optional. The knob 120 may be controlled independently of any fastening mechanism 112, such that securing the device 100 to the patient and adjusting the pressure to the pre-inflated pad 118 are performed independent of one another.

Figure 3A:
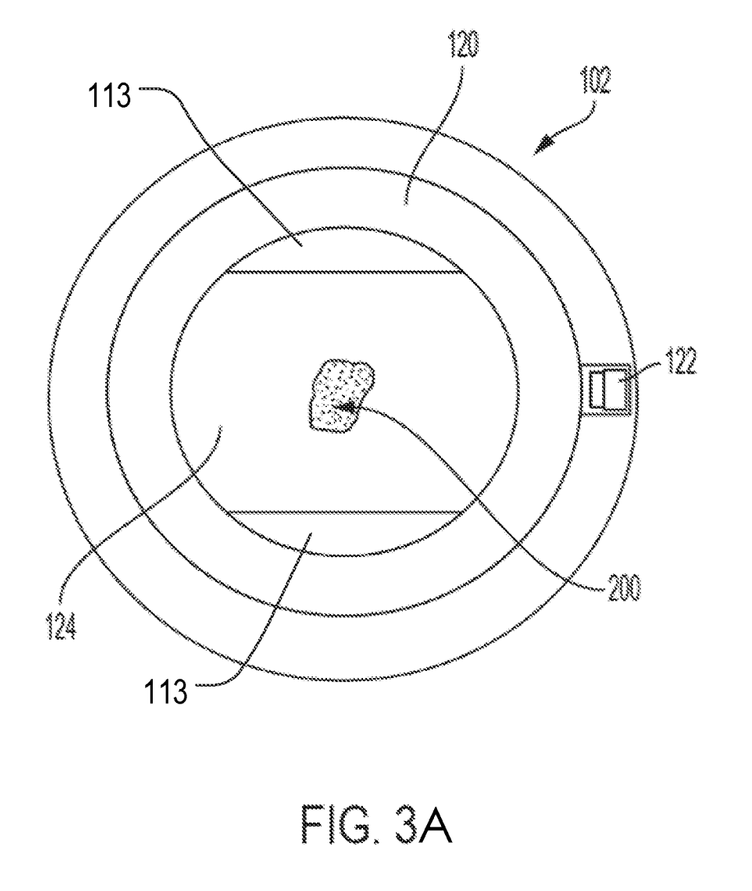
FIG. 3A depicts a top view of a portion of the device shown in FIG. 1, in accordance with an embodiment.
Figure 3B:
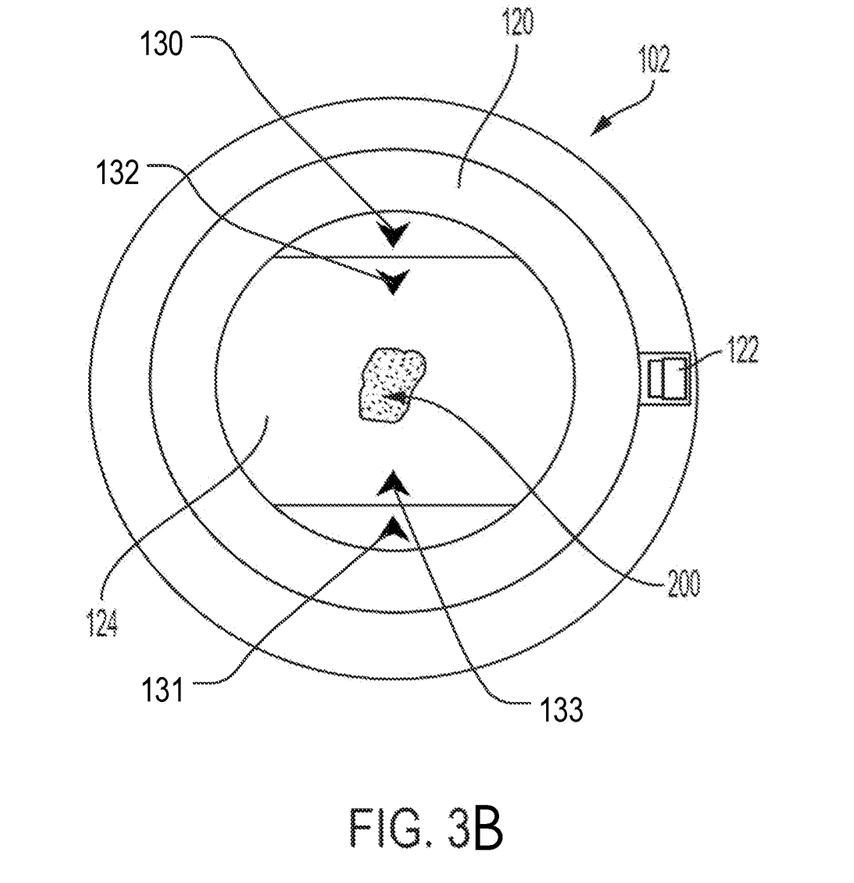
FIG. 3B depicts a top view of a portion of the device shown in FIG. 1, in accordance with another embodiment.

In some embodiments, the knob 120 includes a transparent portion. FIG. 3 depicts a top view of a portion of the device shown in FIG. 1, which shows a transparent portion 124, through which the access site of the patient can be viewed. Additionally, in some embodiments, the transparent portion 124 may include a magnification element or device to provide a magnification of the access site to more easily determine the status of bleeding at the access site. In some embodiments, the transparent portion 124 may include one or more markers, which will be described in detail with respect to FIG. 3B. Additionally, in some embodiments, the knob 120 may be hollow.

It should be understood that in alternate embodiments, the knob 120 may be replaced with any other suitable mechanism for applying a force to the pre-inflated pad 118, such as, for example, a spring action button.

As mentioned above, in some embodiments, the incremental and decremental pressures applied to the pre-inflated pad 118 may be controlled by a releasable and reusable cable tie mechanism or drawstring and cord lock mechanism positioned at the side of the wrist or top of the wrist opposite the access site of the patient.

Figure 4:
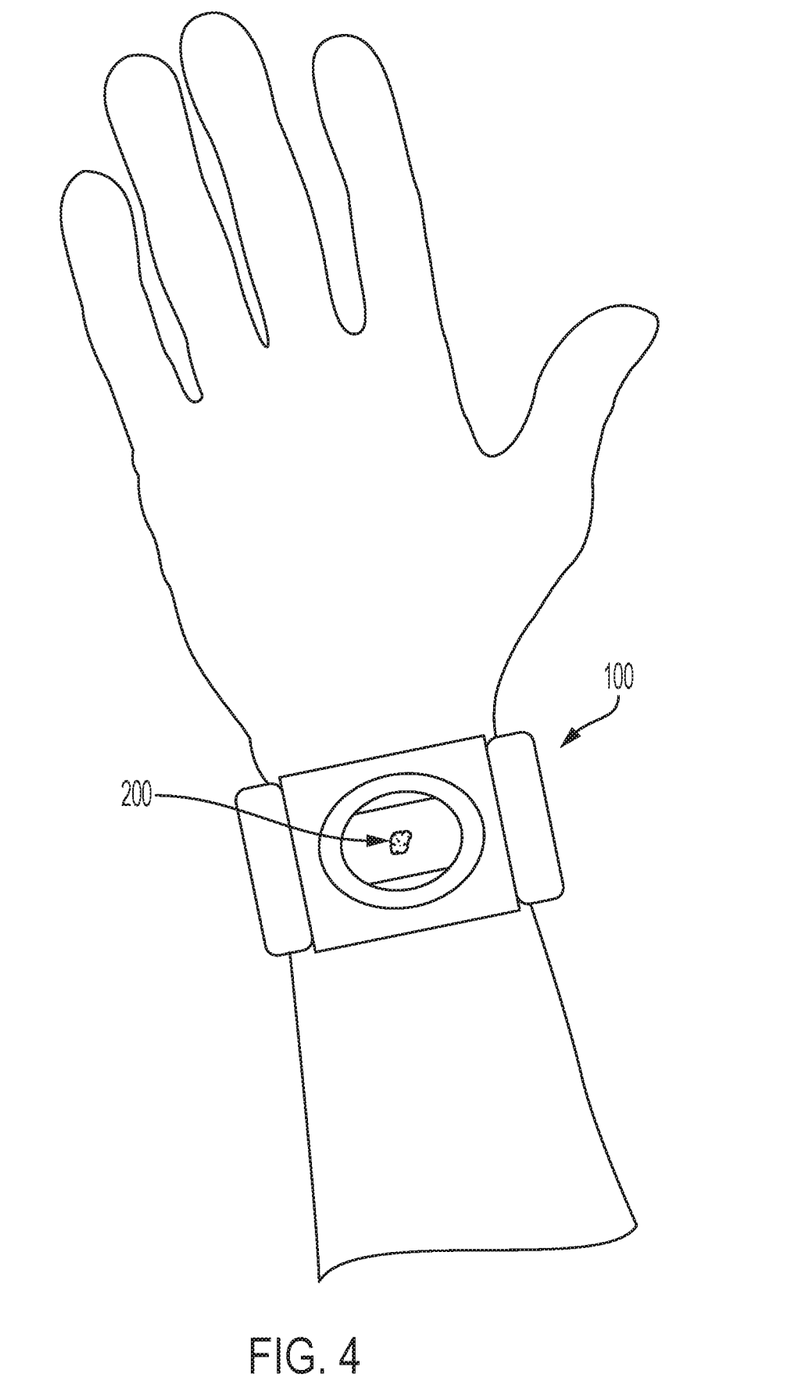
FIG. 4 depicts the device of FIG. 1 positioned on a patient, in accordance with an embodiment.

In operation, a user may apply the pre-inflated pad 118 of the disposable cuff 104 to the access site 200 of a patient. FIG. 4 depicts the hemostasis pressure device 100 of FIG. 1 positioned on a wrist of a patient. The disposable cuff 104 is positioned around a wrist of a patient and secured with the adhesive 116 so the cuff 104 is taught, yet still allows for a small amount of bleeding. In some embodiments, no adhesive is used. Next, the reusable component 102 is secured around the cuff 104. In one embodiment, the reusable component 102 may be opened by the fastening mechanism 112 and placed around the cuff 104. In an alternate embodiment, the patient can insert their arm/wrist through the inner housing 108 of the reusable component. In either instance, the pre-inflated pad 118 should be aligned with the marker 113 and the knob 120.

Referring to FIG. 3B, in some embodiments, a plurality of markers 130, 131, 132, and 133 are positioned both on the pre-inflated pad 118 on the disposable cuff and the transparent portion 124 of the knob 120. When properly aligned, markers 130, 131 on the transparent portion 124 are intended to line up directly above and below markers 132, 133 on the pre-inflated pad 118, so that all four markers are aligned and pointing directly toward the center of or next to, such as 4 to 6 millimeters proximal to or distal to, the access site wound 200, as shown in FIG. 3B.

Once the pre-inflated pad 118 is properly aligned within the reusable component 102, the knob 120 can be manually rotated to adjust the pressure applied to the pre-inflated pad 118. For example, the knob 120 can be rotated to increase and/or decrease the pressure until the appropriate pressure has been achieved and bleeding at the access site stops, but normal blood flow through the blood vessel is not impeded. The compression can then be decreased after a given time interval (for example, pressure could be decreased every 10 minutes) by rotating the knob 120 by specific degree turn intervals (e.g., by 10 to 30 degree intervals). After a given amount of time, hemostasis should be achieved, and the hemostasis pressure device 100 can be removed. A shorter hemostasis time may be achieved with a hemostatic agent coating on the pre-inflated compression pad component 118.

After use, the disposable cuff 104 is discarded. The reusable component 102 may be sterilized or disinfected, such as by use of an autoclave or vaporized hydrogen peroxide (VHP) processes, if needed, and reused with a new disposable cuff.

Figure 5:
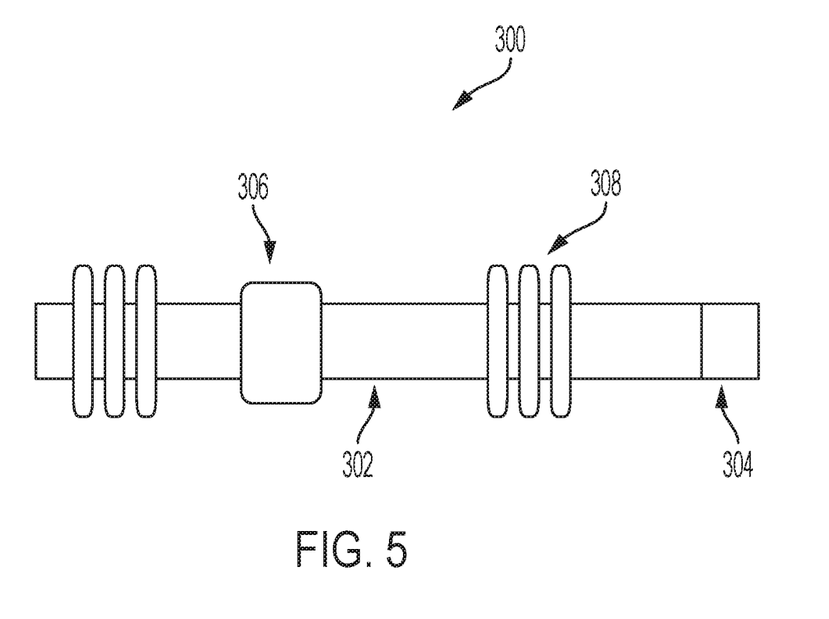
FIG. 5 depicts a top view of an example hemostasis pressure device, in accordance with an embodiment.

FIG. 5 shows an alternate embodiment of a hemostasis pressure device 300. The device 300 is disposable and is similar in structure to the disposable cuff 104. The device 300 includes a flexible strap 302 having adhesive 304, a pad or gauze roll 306, and a plurality of air pocket blisters 308 positioned at one or more locations along the flexible strap. The flexible strap 302 is configured to be placed around a wrist or arm of a patient, with the plurality of air pocket blisters 308 between the flexible strap 302 and the wrist or arm of the patient, and with the gauze roll 306 covering the access site. In some embodiments, the flexible strap 302 is made of a thermoplastic elastomer material. Alternatively, the flexible strap 302 may be made of any suitable material, such as one of or a combination of cotton, polyester, latex, rubber, silicone, or other polymeric materials, for example.

The adhesive 304 is used to affix one end of the strap 302 to the other end of the strap 302 around the patient's wrist. It should be understood that in some embodiments, the adhesive 304 may be replaced with any other suitable fastening mechanism. In some embodiments, there may be an adhesive component at both ends of the strap to be adhered directly to the patient's wrist or arm, or one adhesive may be adhered to the patient's wrist or arm while the other adhesive may be adhered to the strap 302. Additionally, in some embodiments, no adhesive or other fastening mechanism are present.

The gauze roll 306 is infused with a hemostatic agent, such as a hemostatic polymer. The hemostatic agent works quickly to achieve hemostasis. The plurality of air pocket blisters 308 are located along or positioned around the flexible strap 302. In some embodiments, the length of each air pocket blister extends beyond the width of the strap 302. The inflated volume of each air blister allows for significant space between the strap and the patient's wrist, so that each air pocket blister may be easily cut without requiring a scissor or knife blade to be placed between the strap and the patient arm or wrist. In one embodiment, the space between the strap and the patient's wrist may be from about 5 mm to about 15 mm, for example.

In another embodiment, each air blister may be shaped with an elevated protruding tip relative to the base of the blister which touches the arm or wrist of the patient, so that the entirety of the blister may be decompressed via cutting only the protruding tip portion of the air blister (separated from the skin of the patient's arm or wrist by an air gap), which allows for the scissor or knife blade to easily avoid the patient's arm or wrist altogether during decompression. Patient comfort is further improved by reducing shear stress forces at the access site during decompression using the device embodiments and techniques described above, and patient safety is improved by reducing the risk of cutting the patient with the knife or scissor blade.

In some embodiments, the air pocket blisters 308 may be made of silicone. In other embodiments, the air pocket blisters 308 may be made of any suitable material, such as pre-filled gel or water packets, for example. In other embodiments, the air pocket blisters 308 may be dowel sleeves containing dowels and decompression may be achieved via removing one or multiple dowels, which may be made of metal, wood, plastic, or any suitable materials, while compression can be increased at any time by adding one or more dowels.

In operation, a user applies the pad or gauze roll 306 to the access site of a patient. Pressure is applied and the flexible strap 302 is firmly wrapped around the patient's arm or wrist and secured with the adhesive 304 to stop bleeding. In some embodiments, clamps or fasteners are used instead of adhesives. After about 10 minutes, one or more of the air pocket blisters 308 may be cut, deflated, removed or otherwise deactivated from providing pressure, to gradually decrease the compression applied to the access site. One or more additional air pocket blisters 308 are deactivated in fixed intervals, such as about 10 minute intervals. If the pressure becomes too small and bleeding is observed at the access site, a dowel, pre-inflated air pocket blister, or other similar object may be placed into or under one of the cut (decompressed) air pocket blisters or placed at another location between the strap and the patient's arm or wrist to increase the pressure.

The present application provides a number of advantages, including the reduction of waste due to the reusable component of the device. Furthermore, the device provides a low pressure and a low cost solution in achieving patent hemostasis. The hemostasis pressure devices disclosed herein also provide a more intuitive and manual control; and improved patient safety and comfort compared to prior art patent hemostasis devices. The hemostasis pressure devices disclosed herein also allow for decompression and compression at the access site of the patient without compromising the structural integrity of the disposable component or strap directly in contact with the patient.

While a number of exemplary aspects and embodiments have been discussed above, those of skill in the art will recognize that still further modifications, permutations, additions and sub-combinations thereof of the features of the disclosed embodiments are still possible. It is therefore intended that the following appended claims and claims hereafter introduced are interpreted to include all such modifications, permutations, additions and sub-combinations as are within their true spirit and scope.

The invention claimed is:

1. A hemostasis pressure device comprising:
   a reusable component having an outer housing and an inner housing;
   a disposable cuff positioned within the inner housing, the disposable cuff comprising a pre-inflated pad, wherein the pre-inflated pad is configured to be placed at an access site of a patient; and
   a knob secured to the reusable component, the knob having a portion through which the access site can be viewed;
   wherein the knob is configured to control a pressure applied to the pre-inflated pads; and wherein the inner housing is formed by a first end portion overlapping a second end portion, wherein the knob contacts the overlapping first and second end portions, and wherein the overlapping end portions are configured to cause the hemostasis pressure device to distribute incremental and decremental pressure evenly across at least the entirety of the access site location.

2. The hemostasis pressure device of claim 1, wherein the knob is rotatable to adjust the pressure applied to the pre-inflated pad.

3. The hemostasis pressure device of claim 2, wherein rotation of the knob causes the incremental or decremental pressures to be applied to the inner housing.

4. The hemostasis pressure device of claim 3, wherein the inner housing is configured to receive an arm or wrist of the patient therethrough.

5. The hemostasis pressure device of claim 1, wherein the knob further includes a knob lock configured to lock the knob in a position.

6. The hemostasis pressure device of claim 1, further comprising one or more markers to indicate correct positioning of the reusable component and the disposable cuff.

7. The hemostasis pressure device of claim 1, wherein the disposable cuff further comprises a flexible strap including a fastening mechanism and the pre-inflated pad.

8. The hemostasis pressure device of claim 1, wherein the pre-inflated pad is configured to be inflated to a predetermined pressure or filled to a predetermined volume.

9. The hemostasis pressure device of claim 1, wherein the pre-inflated pad includes or is coated with a hemostatic agent.

10. The hemostasis pressure device of claim 1, wherein the reusable component is made of a rigid material.

11. A hemostasis pressure device comprising:
    a reusable component having an outer housing and an inner housing, wherein the inner housing is formed by a first end portion overlapping a second end portion;
    a disposable cuff positioned within the inner housing, the disposable cuff comprising a pre-inflated pad, wherein the pre-inflated pad is configured to be placed at an access site of a patient; and
    a knob secured to the reusable component, the knob having a portion through which the access site can be viewed;
    wherein the knob is configured to control a pressure applied to the pre-inflated pad; and
    wherein the knob contacts the overlapping first and second end portions, and wherein the overlapping end portions are configured to cause the hemostasis pressure device to distribute incremental and decremental pressure evenly across at least the entirety of the access site location.

12. The hemostasis pressure device of claim 11, wherein the inner housing is configured to receive an arm or wrist of the patient therethrough.

13. The hemostasis pressure device of claim 11, wherein one or more of the first and second overlapping end portions is transparent.

14. The hemostasis pressure device of claim 11, wherein the reusable component is made of a rigid material.

15. The hemostasis pressure device of claim 11, wherein the pre-inflated pad includes or is coated with a hemostatic agent.

16. The hemostasis pressure device of claim 11, further comprising one or more markers to indicate correct positioning of the reusable component and the disposable cuff.

17. A hemostasis pressure device comprising:
    a reusable component having an outer housing surrounding an inner housing, wherein the outer housing and the inner housing are substantially concentric;

a disposable cuff positioned within the inner housing, the disposable cuff comprising a pre-inflated pad, wherein the pre-inflated pad is configured to be placed at an access site of a patient; and a knob secured to the reusable component, the knob having a portion through which the access site can be viewed;

wherein the knob is configured to control a pressure applied to the pre-inflated pad.

18. The hemostasis pressure device of claim 17, wherein the inner housing is configured to receive an arm or wrist of the patient therethrough.

19. The hemostasis pressure device of claim 17, wherein the site through which the access site can be viewed may include a magnification element.

20. The hemostasis pressure device of claim 17, wherein the pre-inflated pad includes or is coated with a hemostatic agent.

* * * * *